(12) United States Patent
Roeder et al.

(10) Patent No.: US 10,729,415 B2
(45) Date of Patent: Aug. 4, 2020

(54) VIBRATING MEDICAL DEVICE ASSEMBLY AND METHOD OF RETRIEVING EMBEDDED IMPLANTABLE DEVICE

(71) Applicant: Cook Medical Technologies LLC, Bloomington, IN (US)

(72) Inventors: Rebecca Roeder, Bloomington, IN (US); Joshua F. Krieger, Topsfield, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 399 days.

(21) Appl. No.: 15/484,770

(22) Filed: Apr. 11, 2017

(65) Prior Publication Data
US 2017/0333016 A1 Nov. 23, 2017

Related U.S. Application Data

(60) Provisional application No. 62/339,326, filed on May 20, 2016.

(51) Int. Cl.
| | | |
|---|---|---|
| A61B 17/00 | (2006.01) | |
| A61B 17/22 | (2006.01) | |
| A61F 2/01 | (2006.01) | |
| A61N 1/05 | (2006.01) | |

(52) U.S. Cl.
CPC .. *A61B 17/00234* (2013.01); *A61B 17/22031* (2013.01); *A61F 2/01* (2013.01); *A61N 1/056* (2013.01); *A61B 2017/00358* (2013.01); *A61B 2017/22014* (2013.01); *A61B 2017/22035* (2013.01); *A61F 2002/011* (2013.01); *A61F 2002/016* (2013.01); *A61F 2230/0067* (2013.01)

(58) Field of Classification Search
CPC ........... A61B 2017/00358; A61B 2017/22035; A61B 17/32056; A61F 2002/011; A61F 2002/01; A61N 1/056; A61N 1/057; A61N 1/0573; A61N 2001/0578; A61N 2001/058
See application file for complete search history.

(56) References Cited

U.S. PATENT DOCUMENTS

| | | |
|---|---|---|
| 4,920,954 A | 5/1990 | Alliger et al. |
| 5,330,481 A | 7/1994 | Hood et al. |
| 5,713,848 A | 2/1998 | Dubrul et al. |

(Continued)

FOREIGN PATENT DOCUMENTS

WO 2010023671 3/2010

OTHER PUBLICATIONS

European Patent Office, European Search Report for Application No. 17171789.5, Published Oct. 12, 2017, Munich Germany.

*Primary Examiner* — Sarah A Simpson
(74) *Attorney, Agent, or Firm* — Liell & McNeil

(57) ABSTRACT

An implanted device, such as an inferior vena cava filter, that is partially embedded in soft tissue is retrieved by coupling a vibration device to the implanted device. The implanted device is disembedded from the soft tissue at least in part by generating a vibration with a vibration generator, transmitting the vibration along the vibration transmission apparatus to the implanted device, and vibrating the implanted device. The implanted device is then moved away from the embedding site. A medical device assembly includes the vibration generator, the implantable device and the vibration transmission apparatus.

14 Claims, 2 Drawing Sheets

(56) References Cited

U.S. PATENT DOCUMENTS

| | | |
|---|---|---|
| 6,440,077 B1 | 8/2002 | Jung et al. |
| 6,660,013 B2 | 12/2003 | Rabiner et al. |
| 7,686,825 B2 | 3/2010 | Hauser et al. |
| 8,273,253 B2 | 9/2012 | Curran |
| 8,852,194 B2 | 10/2014 | Young |
| 2007/0093744 A1 | 4/2007 | Elmaleh |
| 2009/0163926 A1 | 6/2009 | Sos |
| 2009/0292307 A1 | 11/2009 | Razack |
| 2010/0100139 A1* | 4/2010 | Young .................. A61F 2/4603 606/86 A |
| 2011/0208319 A1 | 8/2011 | Laster |
| 2013/0150695 A1* | 6/2013 | Biela ...................... A61B 5/042 600/374 |
| 2013/0267848 A1* | 10/2013 | Fearnot ................ A61B 8/0841 600/439 |
| 2014/0172008 A1* | 6/2014 | McKinnis .............. A61B 17/50 606/200 |
| 2014/0248581 A1 | 9/2014 | Petersen et al. |
| 2015/0367123 A1 | 12/2015 | Kalmann et al. |

\* cited by examiner

VIBRATING MEDICAL DEVICE ASSEMBLY AND METHOD OF RETRIEVING EMBEDDED IMPLANTABLE DEVICE

TECHNICAL FIELD

The present disclosure relates generally to disembedding and possibly retrieving implantable devices embedded in soft tissue, and more particularly to utilizing a vibration to free an implanted device that has become embedded in soft tissue.

BACKGROUND

Retrieval of inferior vena cava (IVC) filters can be challenging, especially in cases where the filter has indwelt for long periods of time. The filter struts can embed in the wall of the IVC, or the filter tip can tilt and become embedded within the IVC wall. Once the filter has embedded into soft tissue, retrieval becomes significantly more difficult and risky for the patient. Current retrieval methods often involve significant force or complex cutting, and are often high risk for the patient. Other implantable devices, such as pacemaker leads or migrating stents can be difficult to retrieve when becoming embedded into soft tissue.

The present disclosure is directed toward one or more of the problems set forth above.

SUMMARY

In one aspect, a medical device assembly includes a vibration transmission apparatus with one end coupled to a vibration generator, and an opposite end in contact with an implantable device. The implantable device is shaped for temporary or permanent implantation in a blood vessel.

In another aspect, a method of retrieving an implanted device that is partially embedded in soft tissue at a site includes coupling a vibration transmission apparatus to the implanted device. The implanted device is disembedded from the soft tissue at least in part by generating a vibration with a vibration generator, transmitting the vibration along the vibration transmission apparatus to the implanted device, and vibrating the implanted device. The implanted device is then moved away from the site.

DETAILED DESCRIPTION

Figure 1:
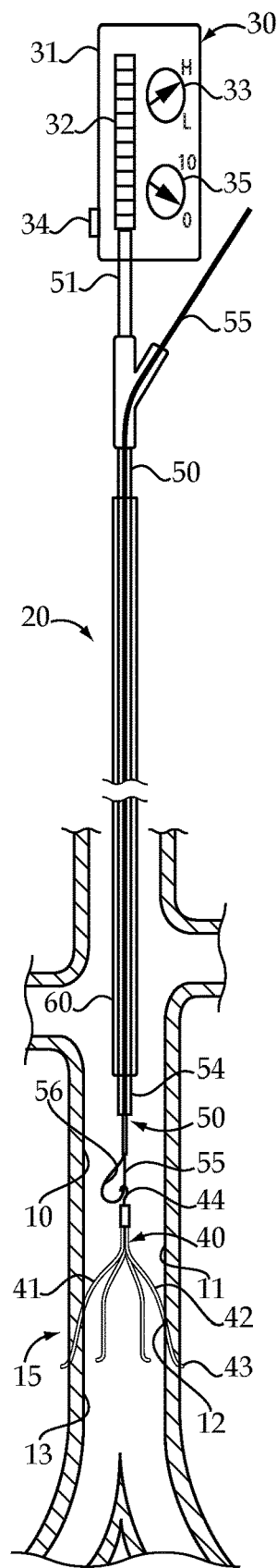
FIG. 1 is a schematic view of the medical device assembly in the early stages of a retrieval process.

Referring initially to FIGS. 1-4, a medical device assembly 20 includes a vibration generator 30, which may be suitable for generating ultrasonic vibrations in a manner known in the art. In the illustrated embodiment, vibration generator 30 includes a piezo stack actuator 32 positioned in a handle 31. Vibration generator 30 may also include an activation switch 34, a vibration frequency controller 33 and maybe a vibration magnitude controller 35. Medical device assembly 20 also includes an implantable device 40 that is shaped for temporary or permanent implantation in a blood vessel 10. In the illustrated embodiment, implantable device 40 takes the form of a blood filter 41 in general, and an inferior vena cava filter 42 in particular. Nevertheless, implantable device 40 could be another type of filter, a stent, graft or maybe even a pacemaker lead, or any other known implantable device that is shaped for temporary or permanent implantation in a blood vessel without departing from the present disclosure. Medical device assembly 20 also includes a vibration transmission apparatus 50 with one end 51 coupled to the vibration generator 30, and an opposite end 52 in contact with the implantable device 40. The medical device assembly 20 can be utilized to assist in disembedding the implanted device 40 from soft tissue by causing features of the implanted device (e.g. filter legs 43) to vibrate and act locally like an ultrasonic knife to assist in vibrating the implanted device 40 out of the soft tissue in which it is embedded. As used in this disclosure, "coupling" can be as simple as contact or as complex as a simultaneous push/pull connection facilitated by a snare 55 and cannula 54. Those skilled in the art will appreciate that a specialized capture mechanism tailored to an individual filter type could be considered to be a "snare" in the context of the present disclosure.

Figure 2:
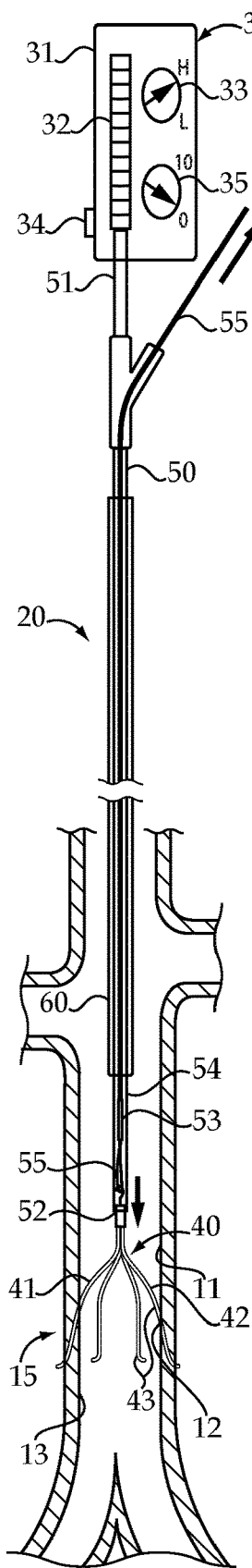
FIG. 2 is a schematic view similar to FIG. 1 except later in the retrieval process according to one aspect of the present disclosure.
Figure 3:
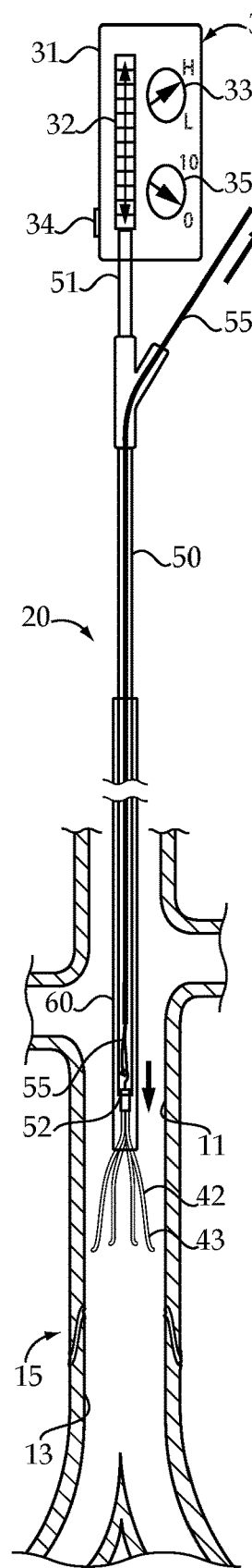
FIG. 3 is a schematic view of the medical device assembly after the implantable device has become disembedded.
Figure 4:
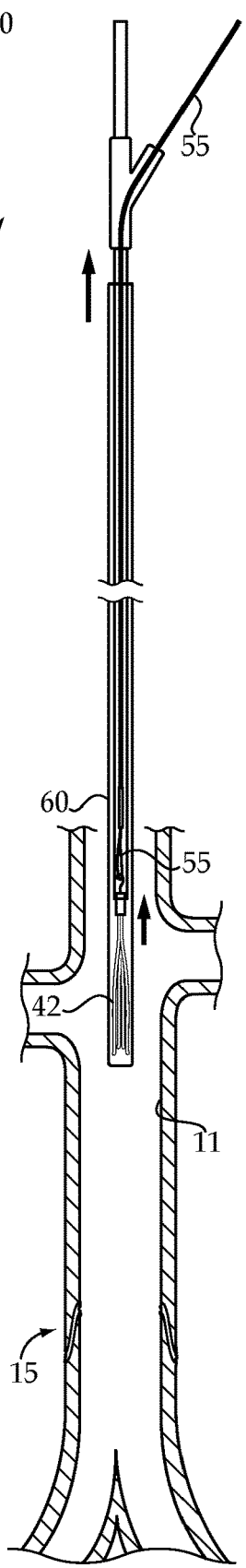
FIG. 4 is a schematic view similar to FIGS. 1-3 showing the implantable device being moved away from the embedding site.

In the illustrated embodiment, the vibration transmission apparatus 50 includes a canula 54 and a tension member 53, which may take the form of a snare 55 or a loop 56 snared to the end 44 of the inferior vena cava filter 42. In the illustrated embodiment, at least one leg 43 of the inferior vena cava filter 42 has become embedded in soft tissue 12 in the wall 13 of the inferior vena cava 11. After snaring end 44, the canula 54 may be advanced into contact with the inferior vena cava filter 42 as shown in FIG. 2. While maintaining some tension via the snare 55, the vibration generator 30 may be turned on as shown in FIG. 3. When this occurs, leg(s) 43 of the inferior vena cava filter 42 will vibrate responsive to a vibration transmitted from the vibration generator 30 to the filter 42. As a result, the filter may rapidly and/or more easily free itself from the being embedded in the soft tissue of the blood vessel 10, and permit a conventional retrieval sheath 60 to be advanced over the filter and allow the same to be removed from the patients body as shown in FIG. 4.

Figure 5:
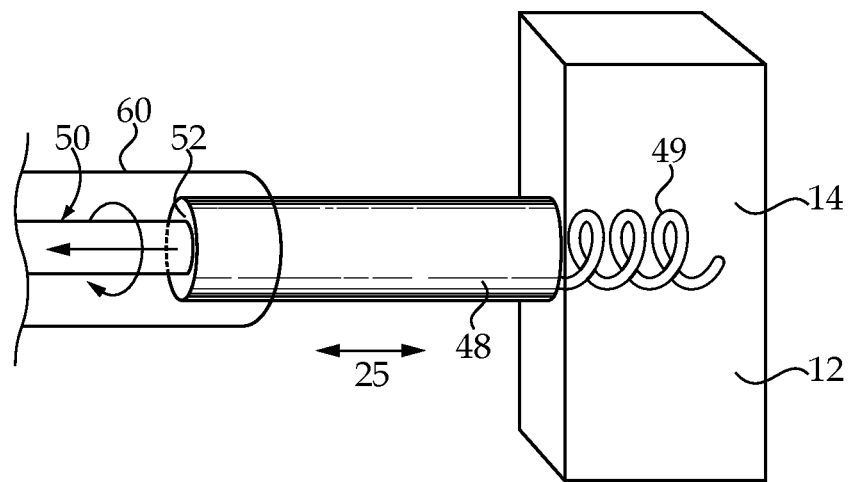
FIG. 5 is a schematic view of a pacemaker retrieval process according to another aspect of the present disclosure.

Referring now to FIG. 5, the concept of the present enclosure may also be applied to removal of an embedded pacemaker lead 48 that is embedded in soft tissue 12 in a patient's myocardium 14. In this case, the vibration transmission apparatus 50 may connect to end 52 of pacemaker lead 48 and then transmit a vibration 25 that permits the fixation thread 49, or other fixation strategy to vibrate and assist in withdrawing pacemaker lead 48 from the soft tissue 12 for removal via sheath 60 in a known manner.

Although not necessary, the vibration 25 may include a predetermined frequency that is correlated to a frequency response mass property of the implantable device 40 and/or mass properties of the tissue in which the device 40 is imbedded. In some instances, it may be advantageous to utilize a vibration frequency that can excite one or more natural frequencies of the implantable device 40. Furthermore, lab testing could allow for identification of certain frequencies that may be best suited for individual known implanted devices. For instance, one frequency may work well for a Tulip type filter, whereas another frequency may perform better for a CELECT™ or a Greenfield™ filter. Accordingly, the vibration frequency controller 33 may be marked with different filter types instead of with numerical frequency selections without departing from the scope of the present disclosure. In such a way, the physician need only determine the type of filter implanted in the patient and then adjust the vibration generator to the frequency best suited for disembedding that particular filter type.

INDUSTRIAL APPLICABILITY

The present disclosure finds general applicability to disembedding, and possibly retrieving, implantable medical devices from a patient. The present disclosure finds specific applicability to disembedding and retrieving embedded inferior vena cava filters. The present disclosure also finds specific applicability to disembedding and retrieval of pacemaker leads.

Referring again to FIGS. 1-4, a method of retrieving an implanted device 40 that is partially embedded in soft tissue 12 at a site 15 includes coupling a vibration transmission apparatus 50 to the implanted device 40. In the illustrated embodiment, in the case of an embedded inferior vena cava filter 42, the process may begin by grasping the hook end 44 of the filter 42 with a loop 56 of a snare 55. Next, a canula 54 is slid along the snare 55 into contact with filter 42 as shown in FIGS. 2 and 3. The implanted device 42 is then disembedded from the soft tissue 12 at least in part by generating a vibration 25 with the vibration generator 30. The vibration 25 is transmitted along the vibration transmission apparatus 54, 55 to the implanted device 42 to cause the implanted device 40 to vibrate. This may be accomplished after canula 54 has been advanced into contact with the filter 42. A snare 55 may be placed in tension while the vibration is transmitted so that when the filter 42 begins to vibrate there is a slight pulling force to help withdraw the same from the soft tissue 12. Thus, while the vibration is being transmitted, the snare 55 may be in tension while the cannula 54 is in compression. The net force on the filter 42 may be a pulling force. After becoming disembedded, the implanted device may be moved away from the site 15, such as by pulling the filter 42 from outside of a sheath 60 into the sheath 60 for removal from the patient's body.

In the illustrated embodiment, the canula 54 is in contact with but not attached to the distal end 44 of the inferior vena cava filter 42. The distal end of the canula may be in contact with one or more of the legs of the filter 42. Canula 54 should be sufficiently rigid that a vibration generated by vibration generator 30 can successfully be transmitted without becoming overly damped before arriving at the implanted device 42 that is embedded in the soft tissue 12. In the illustrated embodiment, the end of the filter 42 may actually be received into the canula 44 when the vibration 25 is transmitted. In some instances, it may be useful to change at least one of a vibration's magnitude and a vibration frequency in order to successfully disembed the implanted device from the surrounding soft tissue 12.

In an alternative embodiment, the implanted device 40 may constitute a pacemaker lead 48. In such a case, depending upon how the pacemaker lead is connected to the wall 13 of the myocardium 14, the disembedding step may include unscrewing the pacemaker lead 48 from the soft tissue 12 while transmitting the vibration 25.

Current vena cava filter retrieval methods can involve significant force or complex cutting, and are high risk for a patient. The present disclosure provides a method of filter retrieval that can minimize tissue damage and reduce patient risk, while also providing a significantly faster and/or easier procedure than current retrieval methods. Furthermore, the filter may be removed with reduced force compared to current retrieval methods.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A method of retrieving an implanted device that is partially embedded in soft tissue at a site comprising the steps of:
    coupling a vibration transmission apparatus to the implanted device;
    disembedding the implanted device from the soft tissue at least in part by generating a vibration in a vibration generator, transmitting the vibration from the vibration generator along the vibration transmission apparatus to the implanted device, and vibrating the implanted device; and
    moving the implanted device away from the site.

2. The method of claim 1 including changing at least one of a vibration magnitude and a vibration frequency during the disembedding step.

3. The method of claim 1 wherein the implanted device is a pacemaker lead.

4. The method of claim 3 wherein the disembedding step includes unscrewing the pacemaker lead from the soft tissue while transmitting the vibration.

5. A method of retrieving an implanted device that is partially embedded in soft tissue at a site comprising the steps of:
    coupling a vibration transmission apparatus to the implanted device;
    disembedding the implanted device from the soft tissue at least in part by generating a vibration with a vibration generator, transmitting the vibration along the vibration transmission apparatus to the implanted device, and vibrating the implanted device;
    moving the implanted device away from the site; and
    wherein the moving step includes pulling the implanted device from outside of a sheath into the sheath.

6. The method of claim 5 wherein the disembedding step includes placing at least a portion of the vibration transmission apparatus in tension while transmitting the vibration.

7. The method of claim 6 wherein the coupling step includes grasping the implanted device with a snare.

8. The method of claim 7 wherein the vibration transmission apparatus includes a cannula with a distal end in contact with the implanted device.

9. The method of claim 8 wherein the implanted device is a blood filter;
    the grasping step includes snaring an end of the blood filter;
    receiving the end from outside the cannula into the cannula; and
    contacting a distal end of the cannula with a leg of the blood filter.

10. A method of retrieving an implanted blood filter that is partially embedded in soft tissue at a site comprising the steps of:

coupling a vibration transmission apparatus to the implanted blood filter;

disembedding the implanted blood filter from the soft tissue at least in part by generating a vibration with a vibration generator located outside a body, transmitting the vibration along the vibration transmission apparatus to the implanted blood filter, and vibrating the implanted blood filter; and moving the blood filter away from the site.

11. The method of claim 10 including a step of placing one portion of the vibration transmission apparatus in tension, and an other portion of the transmission apparatus in compression during the disem bedding step.

12. The method of claim 10 wherein the vibration transmission apparatus includes a cannula; and wherein the disembedding step includes coupling opposite ends of the cannula with the vibration generator and the implanted blood filter, respectively.

13. The method of claim 10 wherein the coupling step includes snaring the implanted blood filter.

14. The method of claim 10 wherein the moving step includes moving the blood filter into a sheath.

* * * * *